US00RE42626E

(19) United States
(12) Reissued Patent
Taylor et al.

(10) Patent Number: US RE42,626 E
(45) Date of Reissued Patent: Aug. 16, 2011

(54) MULTIDIRECTIONAL ADAPTABLE VERTEBRAL OSTEOSYNTSIS DEVICE WITH REDUCED SPACE REQUIREMENT

(75) Inventors: Jean Taylor, Cannes (FR); Bernard Villaret, Croix-Chapeau (FR)

(73) Assignee: Medicrea Technologies, La Rochelle (FR)

(21) Appl. No.: 10/629,788

(22) PCT Filed: Jun. 3, 1998

(86) PCT No.: PCT/FR98/01119

§ 371 (c)(1),
(2), (4) Date: Mar. 2, 2000

(87) PCT Pub. No.: WO98/55038

PCT Pub. Date: Dec. 10, 1998

Related U.S. Patent Documents

Reissue of:
(64) Patent No.: 6,267,765
Issued: Jul. 31, 2001
Appl. No.: 09/445,176
Filed: Mar. 2, 2000

(30) Foreign Application Priority Data

Jun. 3, 1997 (IE) ..... S970411

(51) Int. Cl.
*A61F 5/00* (2006.01)

(52) U.S. Cl. ..... 606/86 A

(58) Field of Classification Search ..... 606/61, 606/60, 69, 72, 73, 86 A, 261, 219, 59, 151, 606/217, 277, 258; 411/383, 388, 389, 397
See application file for complete search history.

(56) References Cited

U.S. PATENT DOCUMENTS

| | | | | | |
|---|---|---|---|---|---|
| 2,190,585 | A | * | 2/1940 | Rhinevault | 269/249 |
| 4,946,458 | A | * | 8/1990 | Harms et al. | 606/305 |
| 5,304,179 | A | * | 4/1994 | Wagner | 606/61 |
| 5,591,166 | A | * | 1/1997 | Bernhardt et al. | 606/266 |
| 5,628,740 | A | * | 5/1997 | Mullane | 606/61 |
| 5,735,851 | A | * | 4/1998 | Errico et al. | 606/61 |
| 5,800,435 | A | * | 9/1998 | Errico et al. | 606/61 |
| 5,851,082 | A | * | 12/1998 | Schmudde et al. | 403/133 |
| 5,891,145 | A | * | 4/1999 | Morrison et al. | 606/266 |

(Continued)

FOREIGN PATENT DOCUMENTS

| | | | | |
|---|---|---|---|---|
| DE | 19512709 | * | 10/1996 | 606/61 |

*Primary Examiner* — Pedro Philogene
(74) *Attorney, Agent, or Firm* — Young & Thompson

(57) ABSTRACT

A vertebral osteosynthesis device includes at least two bone anchoring elements (1) in the vertebral bone structures respectively (S, L5.), a longitudinal linking member (2) between the bone anchoring elements, and connector links (3) between the bone anchoring elements and said linking members. Each bone anchoring element includes a bond fixing part (4), a head (5) to be gripped by a screwing device, a threaded shaft (7) extending the grip head, and a clamping element (8) to be screwed on said shaft to lock together the connector link, the longitudinal linking member and the corresponding bone anchoring element; the threaded shaft (7) is provided at its end with a hinge ball joint (11) in a housing (12) of the grip head (5), enabling a multidirectional adjustment of the shaft (7) and a positioning of the connector link (3) adapted to the vertebral segment configuration (S, L5, . . . Lw) receiving the bone anchoring elements.

25 Claims, 8 Drawing Sheets

U.S. PATENT DOCUMENTS 5,938,663 A * 8/1999 Petreto ..... 606/61
5,984,924 A * 11/1999 Asher et al. ..... 606/264
6,022,350 A * 2/2000 Ganem ..... 606/272
6,123,706 A * 9/2000 Lange ..... 606/264
7,163,538 B2 * 1/2007 Altarac et al. ..... 606/86 A

* cited by examiner

MULTIDIRECTIONAL ADAPTABLE VERTEBRAL OSTEOSYNTSIS DEVICE WITH REDUCED SPACE REQUIREMENT

Matter enclosed in heavy brackets [ ] appears in the original patent but forms no part of this reissue specification; matter printed in italics indicates the additions made by reissue.

FIELD OF THE INVENTION

The subject of the present invention is a spinal, particularly dorso-lumbar, osteosynthesis device.

More specifically, the invention is aimed at a device of the type comprising at least two bone-anchoring elements for anchoring into bone structures of the spine, a member for longitudinally connecting the bone-anchoring elements, and shackles for connecting the bone-anchoring elements and the members for connecting the screws; each bone-anchoring element comprises an anchor for anchoring into the bone, a head for grasping by a screwing tool, a threaded shank extending the head for grasping and a tightening element which can be mounted on this shank to lock together the connector, the longitudinal connecting member and the corresponding bone-anchoring element.

BACKGROUND OF THE INVENTION

Multivertebral, particularly dorso-lumbar, osteosynthesis combines the use of screws or hooks connected together by plates or rods.

The use of plates with appropriate recesses allows the screws a certain amount of travel and allows them to slide along an axis. This is useful when fitting screws which diverge in the sagittal plane.

The use of longitudinal connecting members such as rods for example also allows the bone-anchoring elements, for example screws, to slide along the principal axis of the longitudinal connecting member, and allows screws which diverge in the horizontal plane to be brought onto the same antero-posterior line, and this is by virtue of derotation effects imparted on the rods about an apicocaudal axis, that is to say in the horizontal plane.

However, the bending of the rod that this manoeuvring this must be performed between two vertebral segments which are a sufficient distance apart. Furthermore, one or more successive bending operations are performed only in the same frontal plane. This then results in a deformation transposed into another plane, orthogonal to the first.

The adjusting of the pedicle-screws/rod pair may lead to very high stresses in the system before it is definitely locked.

Special-purpose instruments have therefore been conceived.

Pedicle screws in which the threaded shank is extended rearwards have also been developed, so that the descent of the rod as far as the vertebral implantation base of the screw can be guided, segment by segment.

The other benefit of this type of extended pedicle implant is that it allows equal use either of a plate or of a rod.

There are deformations whose radius of curvature may be short, in one or two segments, but, nonetheless, combined in the three planes, sagittal, horizontal and frontal. Simply bending a rod in a single plane, bringing this rod gradually alongside or performing an overall derotation movement, is then no longer suitable.

This is because the reduction by rotation of the rod in the event of bending in two planes is prohibited by the laws of mechanics.

Reduction of a deformation with a large radius, under such conditions, is in three planes, but is not in any way sequential, and can even less be said to be selective.

These short deformations, which can be reduced partially, have to be considered segment by segment and especially plane by plane before any reduction manoeuvre, particularly partial, can be envisaged.

One vertebra which is off-set in isolation in the frontal sagittal and horizontal planes has to be brought into a condition such that it can undergo reduction in just one plane if necessary, or even with a view to be secured as it is to the adjacent segment under no stress other than the stress induced by neutralization.

To meet these requirements, pedicle screws equipped with a "ball joint" system have been designed and developed.

Thus, the head of a screw may be capped by a U-shaped element thus dubbed a "tulip" which acquires mobility about the principal axis of the screw.

The travel obtained makes it possible, within certain limits, to get around the consequences of an angular offset in the horizontal and/or frontal plane of the pedicle alignment.

This being the case, the bending of the rod is no longer a ruse for roughly aligning a poorly frontally aligned setup.

The surgeon is thus freed of this enormous burden and can implant the pedicle screws along the axis imposed by the topography of the pathological vertebra.

Regional sagittal vertebral statics are observed by virtue of a bending in one plane, aimed at restoring sagittal equilibrium.

Various mechanical solutions are proposed, particularly by successively fitting together elements which culminate in the securing of the screw/ball/rod triplet.

Geometrically complex recesses and the fitting-together of a series of elements allow the advantages of the above described screw/ball-jointed tulip element to be reproduced.

In spite of the considerable progress that this alternative represents, it is appropriate that a critical analysis be made of it, and this analysis can be summarized in three points:

1. The multi-axis U-shaped screws firstly do not allow rod/plate interchangeability, or if they do this entails disassembly rather akin to the "nesting Russian doll" principle.

Furthermore, reduction of an anterolisthesis requires the use of screws with a U, the arms of which are extended backwards, at the expense of requiring far more space. Finally, in order not to stress the tightening elements during traction manoeuvres, use of a special-purpose reduction instrument is recommended but entails stressing the pedicle in tension; all of which cause preliminary weakening.

2. The use of successive spacing pieces may prove tricky, increasing the number of manoeuvres.

The mechanically reliable nature of the immobilization assumes a perfect fit, although such fit is uncertain under operating conditions (firstly the constraints imposed by the process, the interposition of tissue, poor visual inspection, etc.) where the implant is embedded.

The absence of rotational locking between the anchoring part and the multi-axis ball also makes dismantling difficult and sometimes impossible.

3. The special-purpose instruments required involve just as many unknowns which add to the operating time, requiring medical auxiliaries training, and finally make maintenance more involved.

SUMMARY OF THE INVENTION

According to the invention, the threaded shank has a ball end for articulation in a housing of a spherical cup of the head for grasping, allowing the shank to be orientated in many directions, and allowing the connecting shackle to be positioned to suit the configuration of the vertebral segment receiving the bone-anchoring elements, and the ball and the cup have respective centres of rotation which are separated by a distance, giving the device, when tightened using the tightening element, by bearing against the upper part of the head for grasping, a function of returning the bone-anchoring element by transverse force, the connector shackle for this purpose having a spherical bearing surface articulated to a portion of the spherical surface of the cup of the head of the bone-anchoring element.

Depending on the physical characteristics of the connecting shackle, either the surface contact immobilizes the bone-anchoring element and allows the orientation of the bone-anchoring element to be maintained, or the connecting shackle bears against the upper part of the head for grasping, giving the device, upon tightening of the element, a transverse return function.

Thus, among other advantages, the device according to the invention allows the implant to be orientated in many directions using a system which requires a very small amount of space, and allows the bone-anchoring elements to be used either with rods or with plates.

According to one feature of the invention, the threaded shank and the connecting shackle are equipped with means for immobilizing the shank and its ball in terms of rotation once the threaded shank has been introduced into the corresponding through-hole through the shackle.

According to another feature of the invention, the said means comprise at least one rotation-stopping geometry formed between the ball and the contiguous end of the threaded shank, and a second rotation-stopping geometry formed on the interior edge of the hole in the shackle, this second geometry being designed to press against the first geometry once the connecting shackle has been slid along the threaded shank.

According to another feature of the invention, the device also comprises at least one bone-anchoring element comprising an anchoring shape, a head with a transverse collar and a shape for grasping, for screwing and a threaded shank extending the head, the assembly being all of one piece.

BRIEF DESCRIPTION OF THE DRAWINGS

Other particular features and advantages of the invention will emerge from the description which will follow, which is given with reference to the appended drawings which illustrate two embodiments thereof by way of non-limiting examples.

DESCRIPTION OF THE PREFERRED EMBODIMENTS

Figure 1:
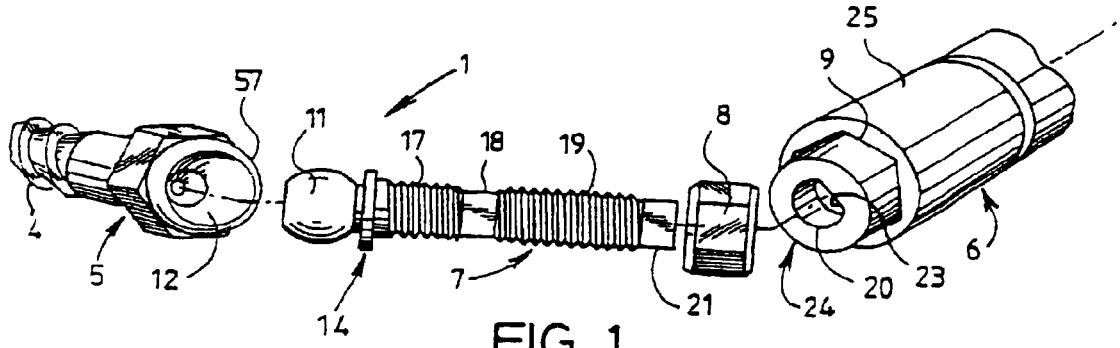
FIG. 1 is a partial perspective view prior to assembly, on an enlarged scale, of a first embodiment of the spinal osteosynthesis device according to the invention.

The spinal osteosynthesis device illustrated in FIGS. 1 to 6 comprises several bone-anchoring elements, consisting, in the example described, of elements 1 for anchoring into the bone of the respective vertebrae, a member for longitudinally connecting the bone-anchoring elements 1, which member consists of a vertebral rod 2, and shackles 3 for connecting the bone-anchoring elements 1 to the vertebral rods 2, there being one shackle 3 per bone-anchoring element 1. Each element 1 comprises a tapered bone-anchoring threaded shank 4, a head 5 for grasping with a screwing tool 6, a mechanical threaded shank 7 extending the head 5. The device is supplemented by a nut 8 which can be screwed onto the threaded shank 7 to lock together the connecting shackle 3, the vertebral rod 2 and the corresponding bone-anchoring element 1.

The head 5 for grasping has a shape which can cooperate with a screwing tool 6, for example a hexagonal outline as depicted, designed to cooperate with a female hexagonal cavity 9 of the tool 6.

The shank 7 has a ball end 11 for articulation in a hemispherical housing 12 of the head 5, in which housing this ball 11 can be held by various assembly techniques, particularly by crimping, welding, etc. The approximately hemispherical housing 12 allows the ball 11 to turn and be mobile in all planes, thus allowing the threaded shank 7 to be orientated in many directions.

The latter and the connecting shackle 3 are fitted with means for immobilizing the shank 7 and its ball 11 in terms of rotation while the nut 8 is being tightened or slackened once the shank 7 has been introduced into a corresponding through-hole 10 through the connecting shackle 3. In the embodiment depicted, these means comprise at least one male rotation-stopping geometry 13 formed on a collar 14 arranged between the ball 11 and the contiguous end of the shank 7, and at least one second, female, rotation-stopping geometry illustrated as a flat 15 formed on the interior edge of the hole 10 in the shackle 3. This second flat 15 is designed to press against the first flat 13 once the shackle 3 has been slid along the threaded shank 7.

As a preference, the collar 14 thus has two diametrically opposed rotation-stopping geometries 13, just one of these geometries 13 being visible in the drawings. The collar 14 thus equipped with the two geometries 13 can fit into the corresponding connecting shackle 3 if the fixture is being used with a vertebral rod 2 or into a plate 16 having similar rotation-stopping geometries (edges of the holes 38, 41, 43 in FIGS. 8 and 9) 13 (FIGS. 8 and 9) if a plate 16 is being used in place of the rod 2 as a member for longitudinally connecting the screws 1.

Figure 2:
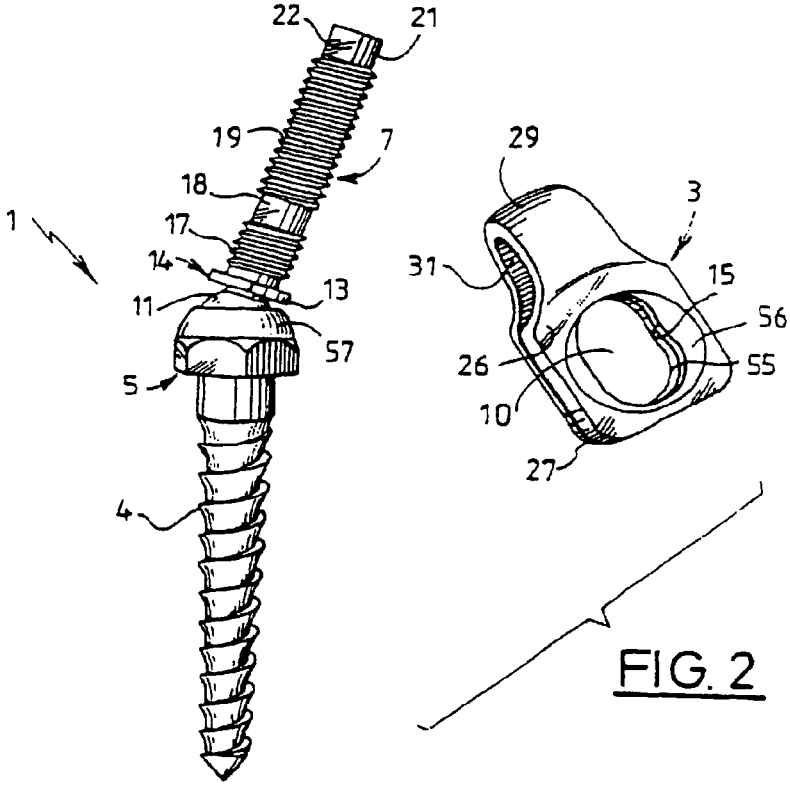
FIG. 2 is a partial perspective view of the device of FIG. 1, showing, on an enlarged scale, a bone-anchoring element with two screw threads and a corresponding shackle for connection to a vertebral rod, not depicted, it being possible for this bone-anchoring element to be, in particular, a screw or a hook.

Beyond the collar 14, the shank 7 has a first cylindrical threaded portion 17, a narrowed portion 18 constituting a break initiator, a second cylindrical threaded portion 19 extended by a plain end part 21 constituting a male shape with an appropriate profile, for example a half-moon profile with a rotation-stopping geometry, hereinafter known as the flat 22 (FIG. 2). This male shape 21 is designed to be able to cooperate with a complementary female shape 20 of the tool 6 formed in the end of a sleeve 24 mounted to slide axially inside a socket 25 at the end of which the hexagonal female cavity 9 is arranged (FIG. 1).

The narrowed portion 18 preferably has a rotation-stopping geometry identical to the fiat 22. This arrangement allows the ball 11 to be immobilized in terms of rotation during an operation of withdrawing the implant, using the tool 6.

Fitting the male shape 21 with its rotation-stopping geometry which may be a flat 22, into the mating female shape 20 with the flats 22 and 23 pressing one against the other, allows the threaded shank 7 to be immobilized in terms of rotation while the nut 8 is being screwed onto the threaded portions 19 and 17 of the shank 7.

Figure 3:
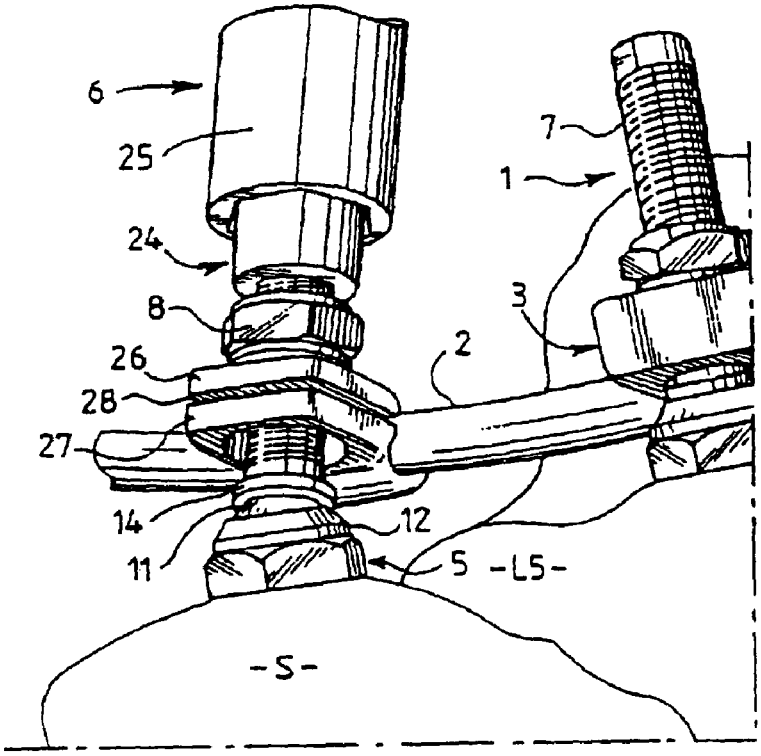
FIG. 3 is a perspective view on an enlarged scale of the device of FIGS. 1 and 2 assembled and fitted to a vertebral segment.

Furthermore, once fitting is complete it is at the narrowed portion 18 that the shank 7 is broken into two parts so that the threaded portion 19 can be removed. Thus, only the threaded portion 17 forms an integral part of the permanent fixture, the second portion 19 having the function only of guiding the descent of the nut 8 as far as the shackle 3 (FIG. 3). During the descent of the nut 8, the fact that the male 22 and female 23 flats of the sleeve 24 are fitted together immobilizes the ball 11 in its housing 12 in terms of rotation.

Figure 13:
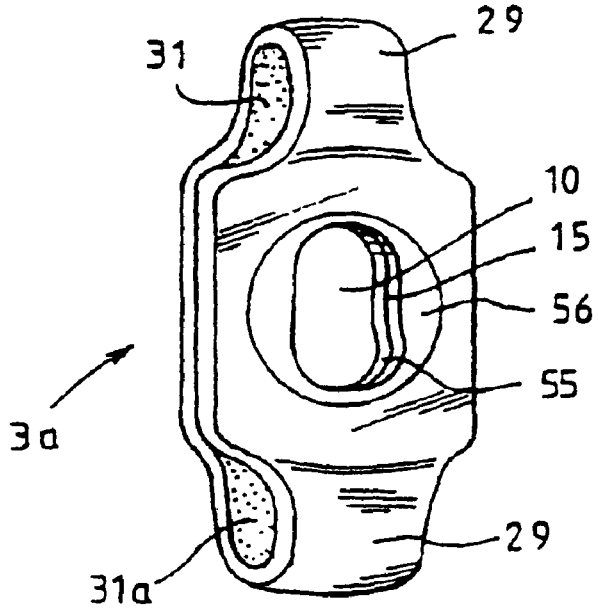
FIG. 13 is a perspective view on an enlarged scale, of a second embodiment of the connecting shackle of FIG. 2.

The connecting shackle 3 consists of two branches 26, 27 bent one over onto the other and separated by a longitudinal slit 28, the hole 10 for the passage of the shank 7 thus being formed in the branches 26, 27 one on each side of the slit 28. The two branches 26, 27 are connected by one or two rounded connecting pieces 29 which delimit one or two cylindrical housings 31 into which one or two cylindrical rods 2 can be introduced (FIG. 13).

Figure 10:
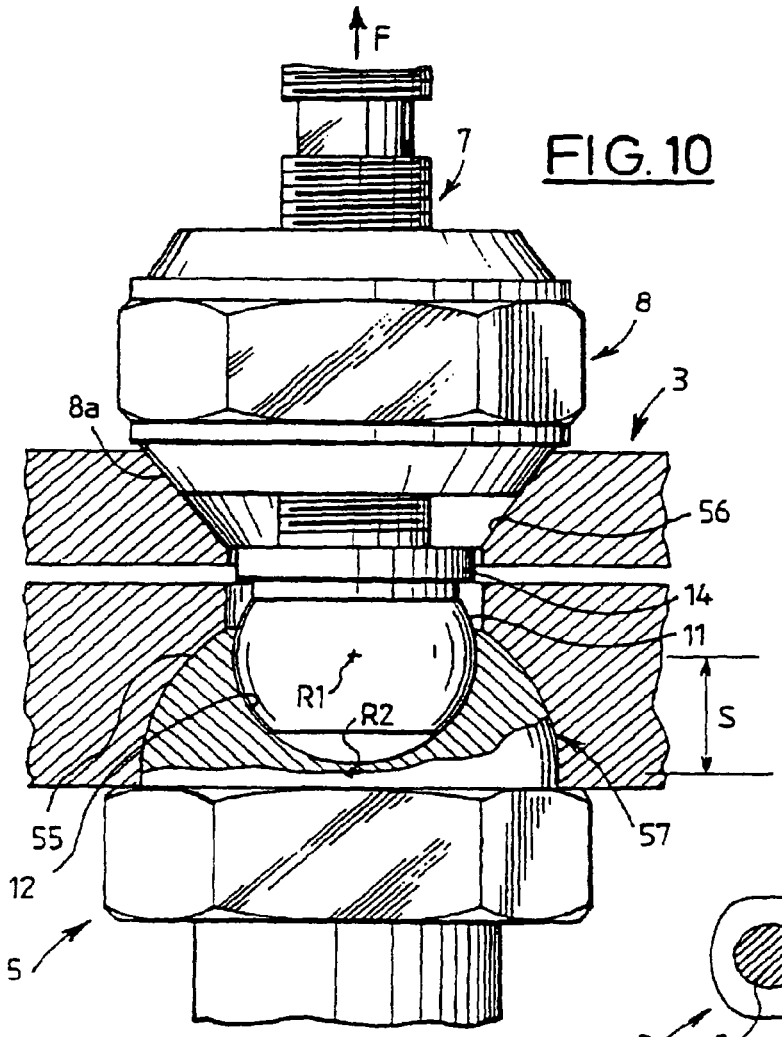
FIG. 10 is a view partly in elevation and partly in section on an enlarged scale of the assembly of a bone-anchoring element, a connecting shackle and a tightening element according to the embodiment of FIGS. 1 to 4, for returning the bone-anchoring element to the axis of the tightening element.
Figure 11:
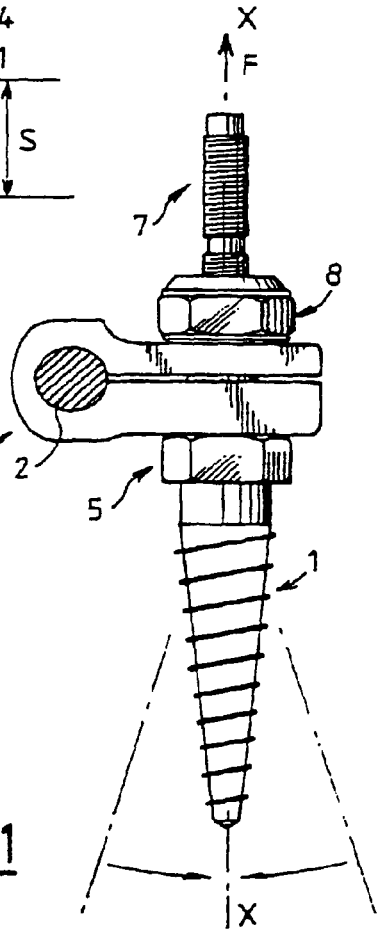
FIG. 11 is a diagrammatic view in elevation on a smaller scale than FIG. 10, of the whole of the corresponding device, illustrating the angular return of the bone-anchoring element to the axis of the tightening element and of the threaded rod during tightening.

FIGS. 10 and 11 illustrate in greater detail the embodiment of the device which has just been described with reference to FIGS. 1 to 3.

Specifically, they show that the sphere or ball 11 of the bone-anchoring element 1 and the spherical cup 57 have respective centres of rotation R1 and R2 which are distinct and separated by a distance S. The surface of the cup 57 of the head 5 is hemispherical and interrupted in its polar region to receive the ball 11, and the associated spherical surface 55 of the shackle 3, with the same radius of curvature as the surface of the hemispherical cup 57, completely covers the latter.

The pressing on the upper part of the head 5 for grasping gives the connecting shackle 3/bone-anchoring element 1 system a function of returning the latter to the axis XX of the tightening nut 8 and of the threaded shank 7 during the tightening manoeuvre using the element 8. Specifically, during this manoeuvre, the element 8 (nut for example), the skirt 8a of which rests against the conical wall 56 of the recess in the nut 8, produces a tensile force F (FIG. 10) which causes a torque C (FIG. 11) which returns the bone-anchoring element 4 towards the longitudinal axis XX of the tightening element 8 and of the threaded shank 7 as the result of a force which is orthogonal to this axis.

Figure 12:
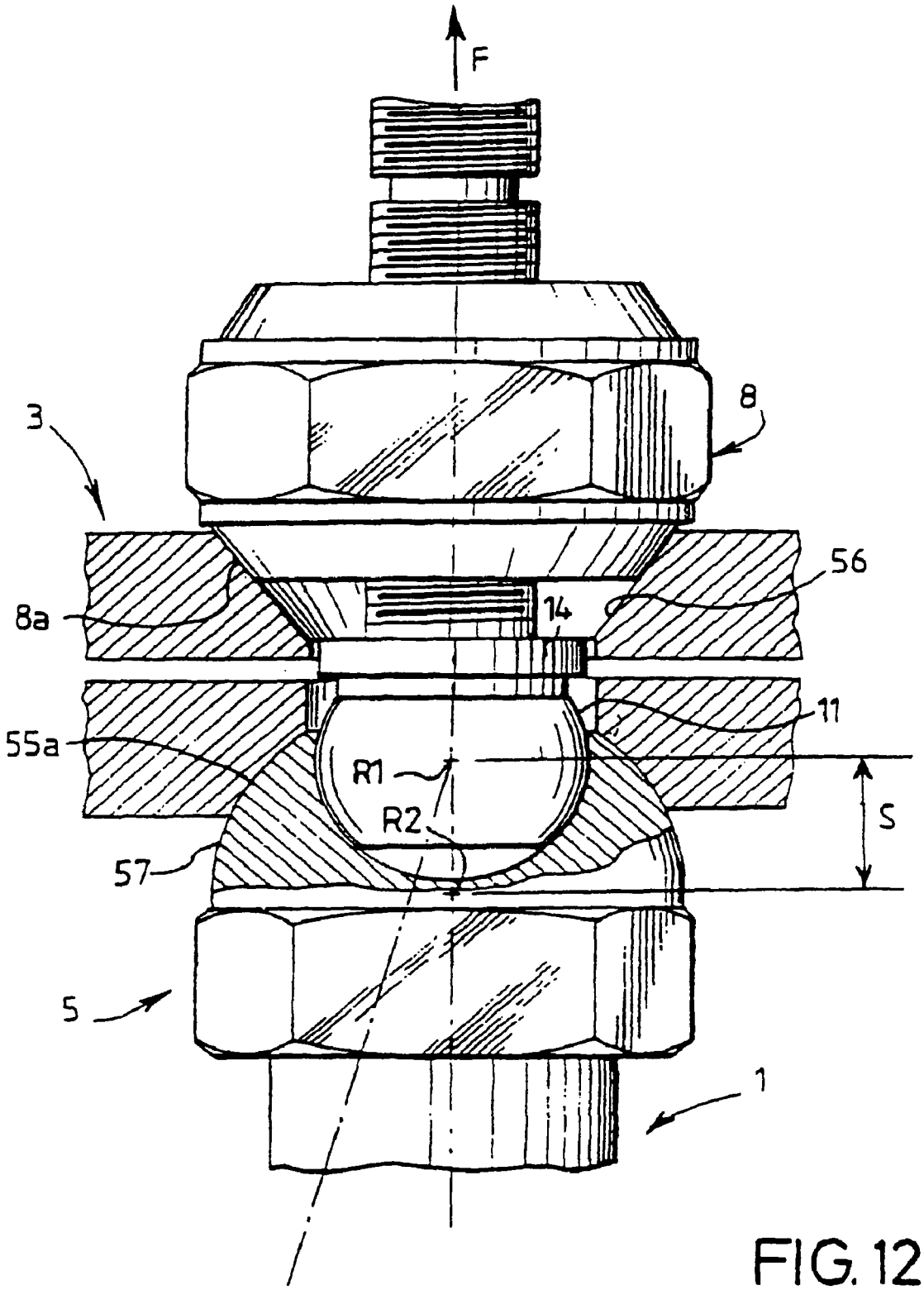
FIG. 12 is a part view similar to FIG. 10 of an alternative form of the device, which is modified so as practically not to provide any appreciable angular return of the bone-anchoring element during tightening.

In the embodiment illustrated in FIG. 12, the spherical surface 55a only partially covers the spherical surface of the cup 57 because the spherical bearing surface 55a is interrupted significantly before the equator of the cup 57. Thus, the tensile force F produced by tightening the nut 8, immobilizes the connecting shackle 3 by surface contact, while at the same time maintaining the orientation of the bone-anchoring element 1.

This possibility of operating using different connectors capable of varying the realignment allows corrections to be planned without having to resort to additional tools.

FIG. 13 illustrates one embodiment of the connecting shackle 3a in which this shackle comprises, on each side of the hole 10, two rounded connecting pieces 29, 29a delimiting two respective housings 31, 31a designed to receive longitudinal connecting members such as vertebral rods.

Figure 14:
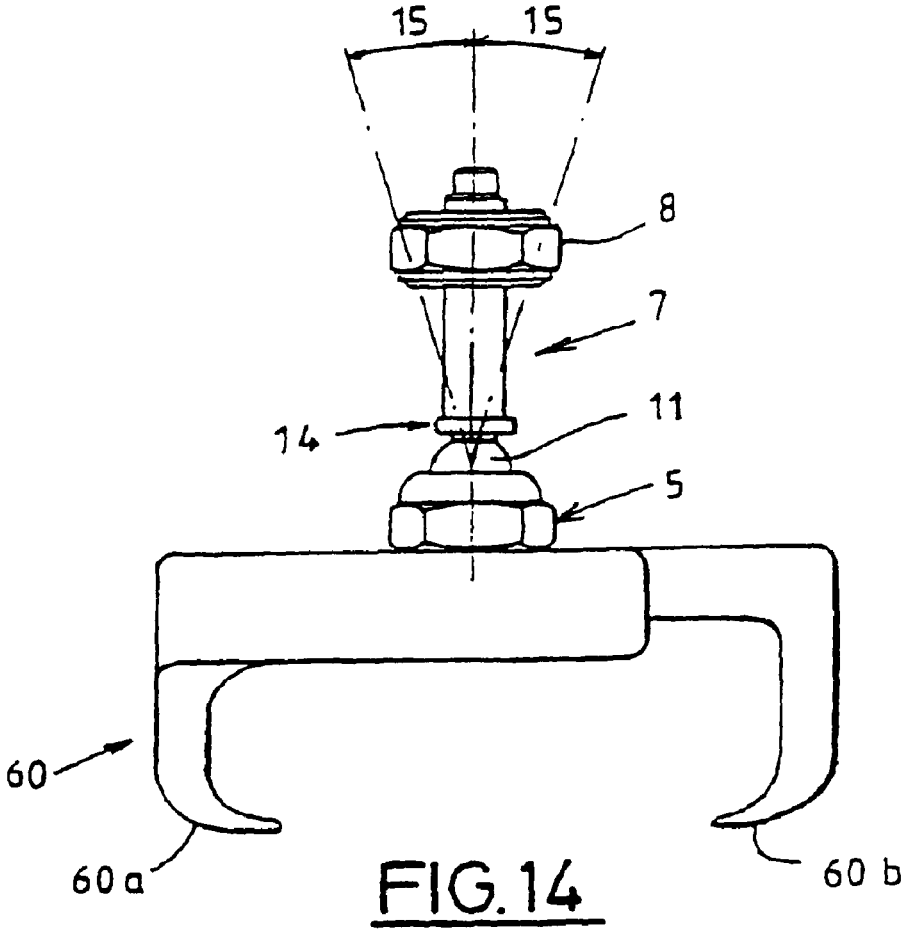
FIG. 14 is a view in elevation on an enlarged scale of a second embodiment of a bone-anchoring element of the device.

FIG. 14 illustrates a second embodiment of the bone-anchoring element, here consisting of a blade-type hook 60 replacing the threaded shank 4 of the previous embodiment, the remainder of the device incidentally being similar to the one in FIGS. 1 and 2, particularly the head 5 for grasping using a screwing tool 6 and the threaded shank 7. The blade-type hook 6 consists, in the way known per se, of two pincers 60a, 60b with curved ends and adjustable relative separation.

Figure 15:
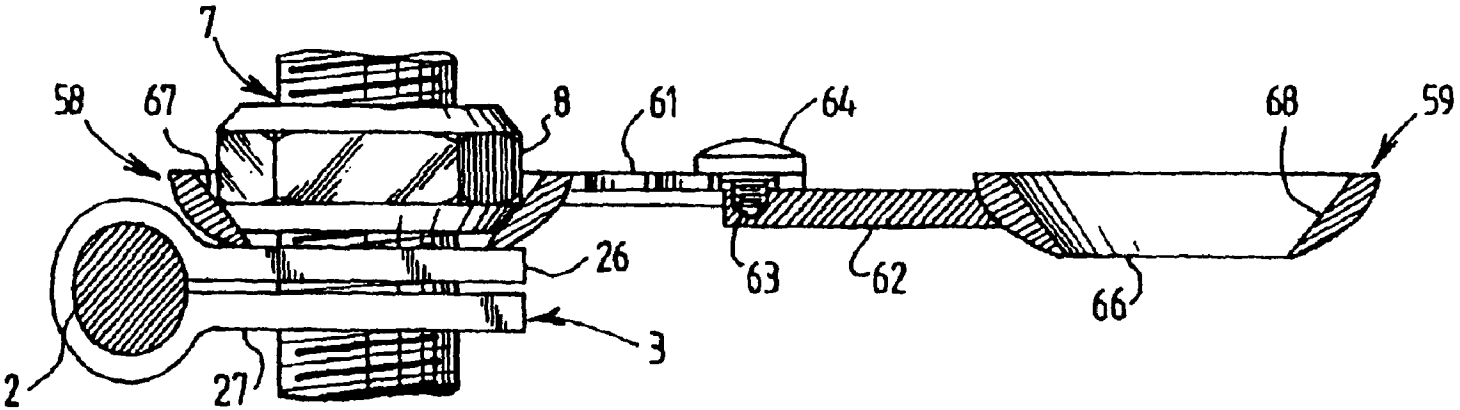
FIG. 15 is a view partly in elevation and partly in section of one embodiment of a system for transversely connecting two bone-anchoring elements, with which the device of FIGS. 1 to 14 may be equipped.
Figure 16:
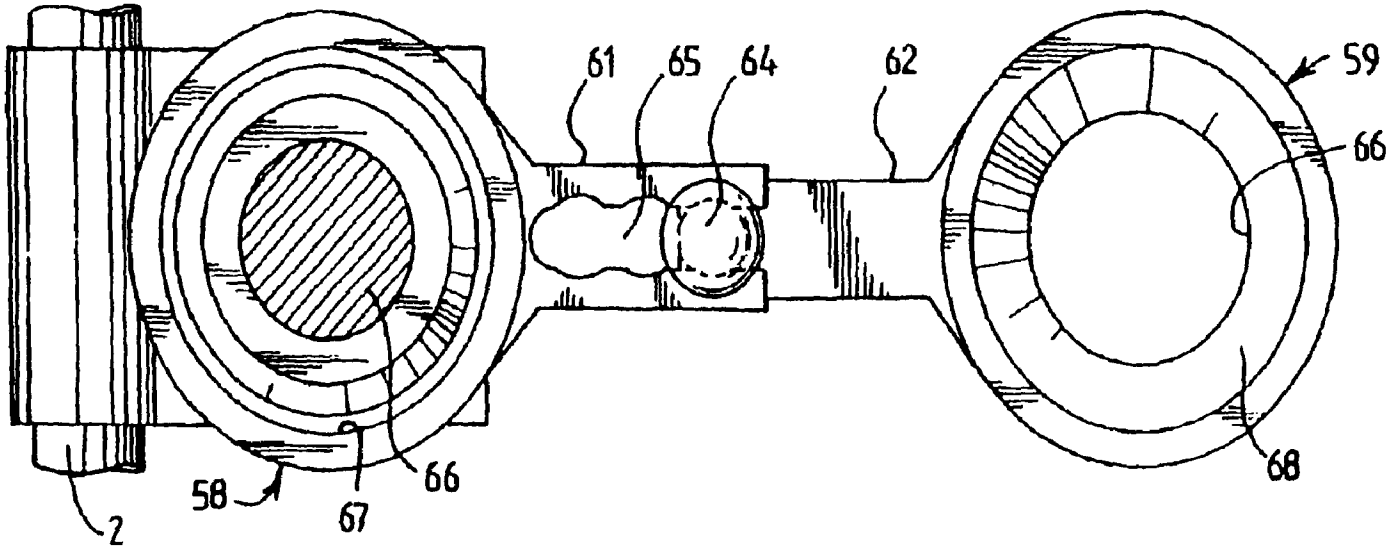
FIG. 16 is a view from above of the transverse connecting system of FIG. 15.

FIGS. 15 and 16 illustrate one possible embodiment of a system for transversely connecting the bone-anchoring elements (1 or 31 or 60). This connecting system is formed of a pair of flared dished elements 58, 59, the bottoms of which are pierced with an opening 66 for the passage of the threaded shank 7. Each dished element 58, 59 is made of one piece with a respective transverse tab 61, 62, the relative position and therefore the separation between the dished elements being adjustable. Adjustment may be achieved for example by means of a screw/nut assembly 63, 64 passing through an elongate slot 65 in one tab 61 and a tapped hole in the other tab 62. Each dished element 58, 59 is interposed between a connecting shackle 3 (or 3a) and a corresponding tightening element 8 which screws into the dished part, resting against its conical wall 67, 68 via its conical skirt 8a.

Figure 8:
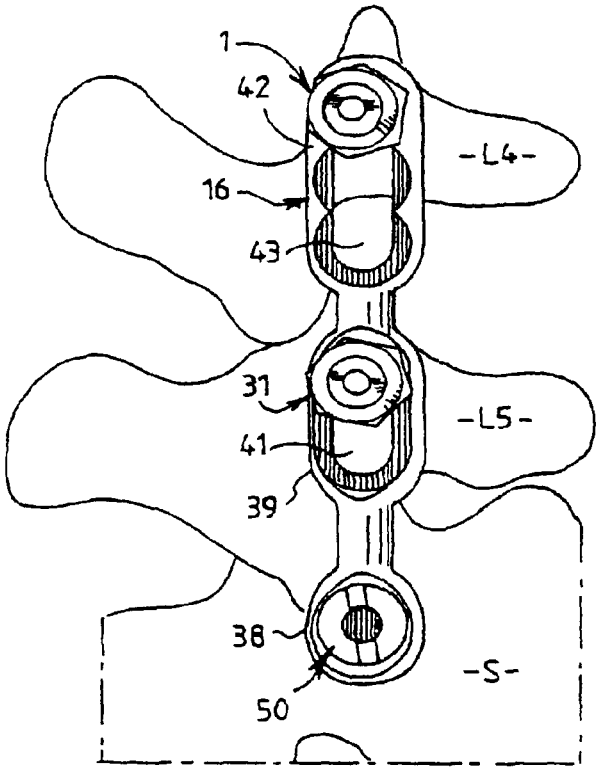
FIG. 8 is a view in elevation from behind of a device with a plate for connecting the bone-anchoring elements and mounted on a dorso-lumbar segment.
Figure 9:
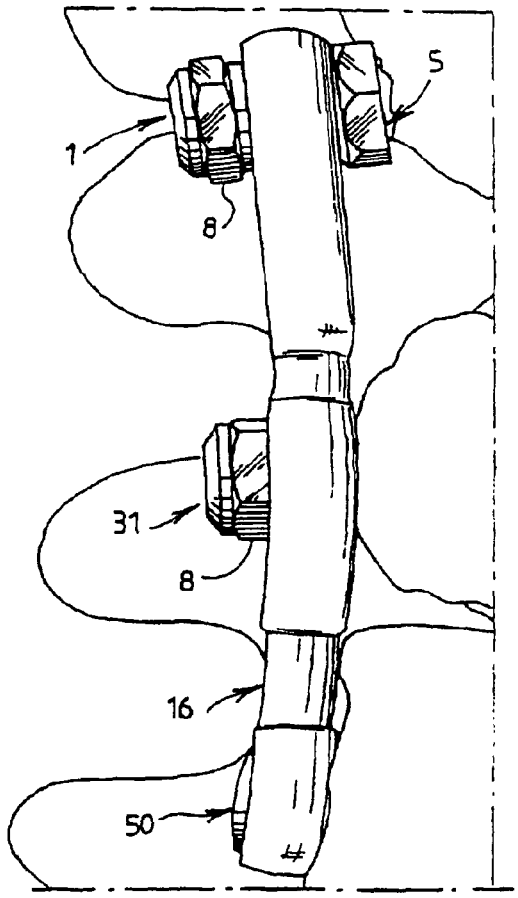
FIG. 9 is a view in elevation in a sagittal plane of the device with a plate of FIG. 8, comprising a bone-anchoring element like the one in FIG. 6.

The ability to orientate the bone-anchoring element 1 with respect to the axis XX, with return (FIGS. 10, 11) or without angular return (FIG. 12) can also be achieved with a similar geometrically complex cavity made in a plate such as 16 (FIGS. 8 and 9, orifice 41, 43).

Once the threaded shank 4 has already been applied to the structure of a vertebra, for example a lumbar vertebra, the shank 7 is orientated towards the corresponding connector 3 already mounted on a vertebral rod 2. Once this has been performed, the tool 6 Allows the shank 7 to be immobilized in terms of rotation using the sleeve 24 while the outer socket 25 allows the tightening element 8 to be screwed as far as its position which immobilizes the assembly, the rotation stopping geometry or geometries 13 of the collar 14 pressing against the corresponding rotation-stopping geometry or geometries 15 of the shackle 3.

Figure 4:
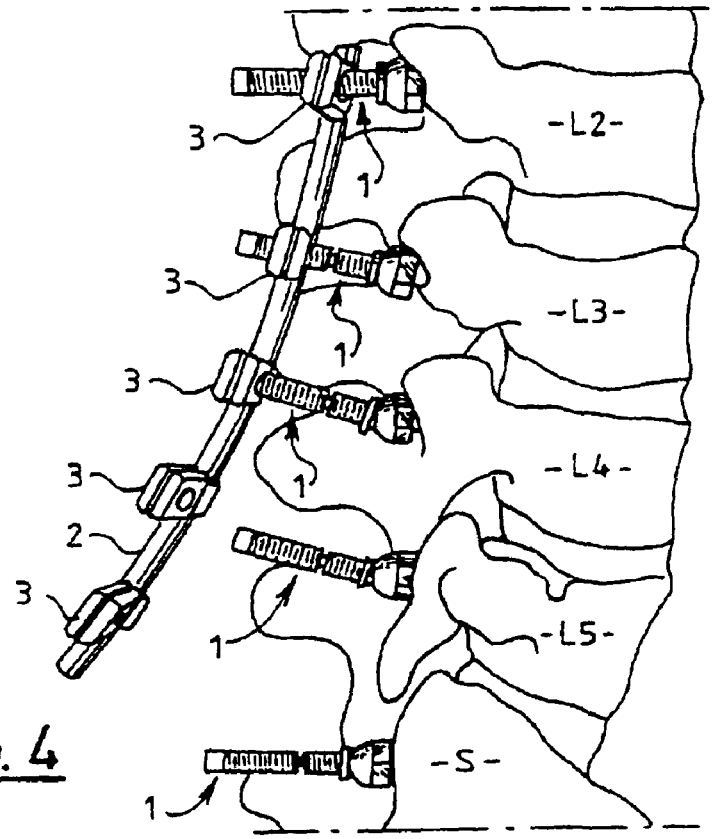
FIG. 4 is an anterolateral elevation view of a dorsolumbar segment with an osteosynthesis device according to the invention, during fitting, some of the connecting shackles with which a vertebral rod is equipped being slipped over the threaded shanks of the corresponding bone-anchoring elements which have already been anchored in the vertebral bony structures.
Figure 5:
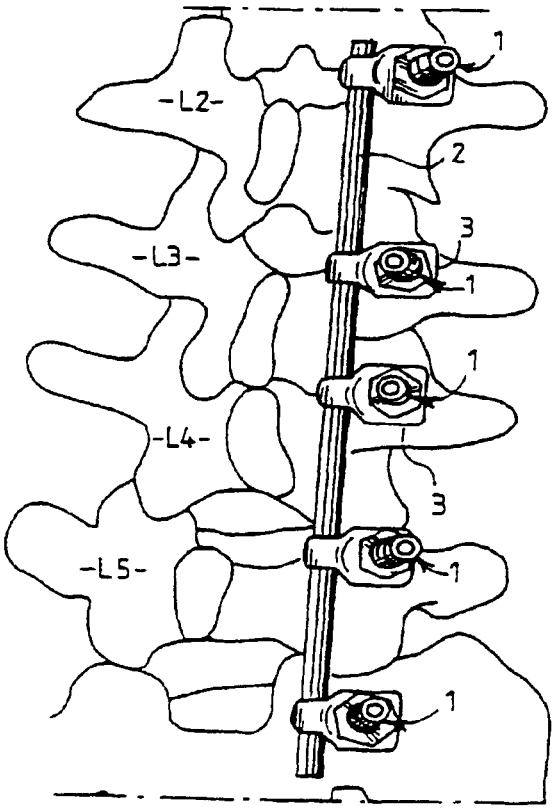
FIG. 5 is a posterior view of the dorso-lumbar segment of FIG. 4 and of the corresponding device, installed.

FIG. 4 illustrates a reduction manoeuvre. The vertebral rod 2 has been bent in the sagittal plane to reproduce the curvature of the lordosis that it is desired to re-establish. The connecting shackles 3 are slipped onto the rod 2 which, via the shackles 3, is guided step by step but without effort, because the ball 11 of each bone-anchoring element 1 allows the extra-pedicle threaded shank 7 to be directed towards the shackle 3 before the rod 2 starts to be brought into contact with the spinal column—namely in the example depicted a dorso-lumbar segment: sacrum S and lumbar vertebrae L5, L4, L3, L2. The descent of the shackle 3 along the threaded shank 7 which constitutes the mobile part of the implant, occurs by virtue of the tightening element 8 (nut), using the wrench which consists of the tool 6 which prevents the ball 11 from turning on itself as explained earlier. The shackle 3 via its underside meets the appropriately orientated collar 14, the two rotation-stopping geometries 22 (flats) 23 meeting, thus immobilizing the ball 11. Specifically, once it is facing the flat 15 of the shackle 3, the collar 14 can no longer turn about its axis. When the two rotation-stopping geometries—the male one 22 and the female one 15—are facing one another, the ball 11 immobilizes itself. The implant has become a single-axis implant.

Figure 6:
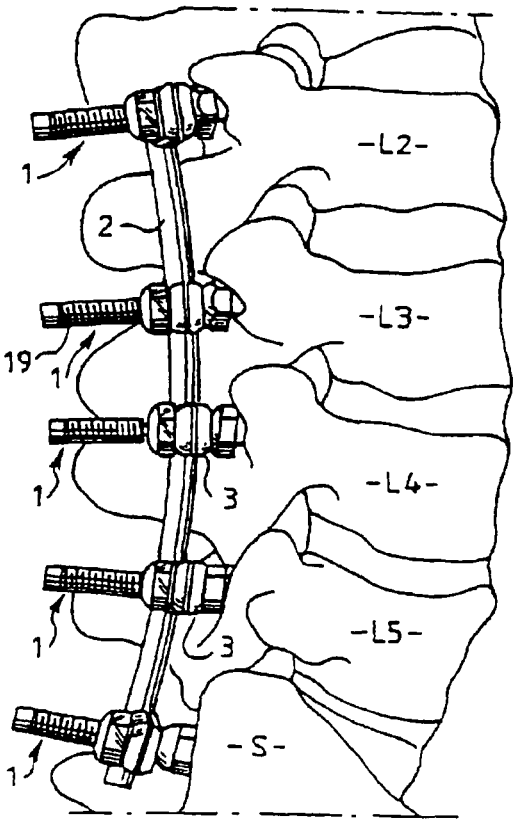
FIG. 6 is anterolateral view of the device of FIG. 5, showing the lumbar lordosis provided by bending the vertebral rod.

In the lombosacral set-up illustrated in FIG. 6, involving the sacrum S and the first four lumbar vertebrae, it can be seen that the physiological lordosis has been restored by curving the rod 2 in the sagittal plane, the extra-pedicle portions consisting of the shanks 7 being orientated correspondingly to adapt to this curvature. Once the set-up has been locked, the posterior portion 19 of each threaded shank 7 is easily broken by virtue of the reduction in cross section formed by the break-initiator region 18. Post-operative X-ray examinations of patients exhibiting lumbar scoliosis make it possible to check that, by virtue of the osteosynthesis device according to the invention, the pedicle implants 1, seen face-on, are not in the same plane and that the lumbar lordosis (side-on) has been restored satisfactorily with, in particular, the reappearance of physiological discal asymmetry, which is essential for creating anatomically correct conditions.

Figure 7:
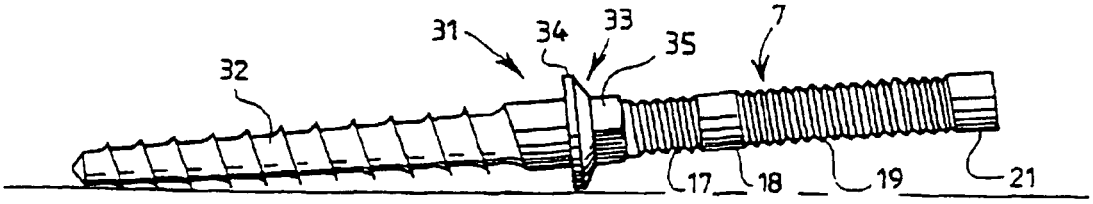
FIG. 7 is a plan view of a one-piece bone-anchoring element without ball, with which the osteosynthesis device according to the invention may be equipped.

FIG. 7 illustrates a second bone-anchoring element 31 (in this example, a screw) which can be used in a device which is not an embodiment according to the invention when this device comprises a plate 16 (FIGS. 8 and 9) or connecting shackles 3.

The bone-anchoring element 31 comprises a threaded anchoring rod 32, a head 33 which has no ball thus making the screw a one-piece screw. The head 33 consists of a transverse collar 34 and a shape 35 for grasping for screwing with an appropriate tool, for example a hexagonal shape. A threaded shank 7 similar to the one of the bone-anchoring element 1 extends the head 33, the assembly being of one piece. Facing the sacrum S the plate 16 has an end part with a circular hole for the passage of a single bone-anchoring element 31, and then, in the region of L5, has a second elongate portion 39 in which there is formed an oblong hole 41 which allows the position of a bone-anchoring element 31 to be adjusted correspondingly between two positions; finally, the plate 16 has a third part 42 of elongate shape in which there is made an oblong passage 43 delimiting three possible positions for the bone-anchoring element 1 depending on the adjustment needed, by virtue of three cut-outs formed on the edges of the passage 43.

The plate 16 which is intended for three spinal segments or stages, S, L5, L4, for example, may be replaced with a plate suited to a different number of stages. For example, in the three-stage set-up of FIGS. 8 and 9, just one bone-anchoring element is multiaxial, and therefore has a ball 11, the other bone-anchoring elements 31 being monoaxial. Each hole (41 . . . ) in the plate 16 may have the same profile as the hole 10 in the connecting shackle 3 for the passage of the bone-anchoring element (FIG. 10). This profile makes it possible to fulfil a function of returning the bone element towards the longitudinal axis of the tightening element and of the threaded shank 7 by means of a force orthogonal to this axis. The collar 34 located in the extension of the intra-pedicle portion of the bone-anchoring element 1 is stationary (FIGS. 8 and 9). It may beneficially provide good support against the vertebra using a so-called "bracket" effect, whereas a bone-anchoring element 1 can beneficially be used to reduce, at segment level, an angle between two contiguous boney structures of the spine.

The multi-axis screw 1 is left free to move at the beginning of the fitting of the tightening element 8 along the threaded shank 7. Next, the sleeve 24 with its half-moon shape 23 immobilizes the ball 11. Using an appropriate movement, the bone-anchoring element 1 is thus positioned in one of the three orifices of the oblong hole 43. The prebending of the plate 16 allows the vertebra L4 to reposition itself in lordosis with respect to the underlying vertebra, without compromising the locking of the plate 16/bone-anchoring element 1 pair, because of the tolerance afforded by the ball 11.

It is possible to use a plate for just two boney structures of the lumbar spine. Prebending this plate allows the vertebra to be tilted in the posterior direction and therefore allows physiological discal asymmetry to be recreated, particularly in the case of the surgical treatment of the so-called "flat back" condition.

Aside from the technical advantages already mentioned, the spinal osteosynthesis device according to the invention exhibits the following advantages:

- the bone-anchoring element 1, 31 is guided by an instrument 6 which instantly normalizes the axis of the pedicle 4, 32 of the bone-anchoring element 1 and its multi-axis extension 7.
- There is a possibility for reduction that is either monoplanar or combined in all three planes.
- Certain operating sequences can be avoided.
- Vertebral reduction by antero-posterior traction using the bone-anchoring element, directly, without additional instruments.
- The orientability of the system can be either maintained or neutralized with equal ease according to the peri-operative requirements by virtue of the dimensional and functional characteristics of the connecting shackles 3 (the combination of the spherical bearing surface 55 or 55a with the spherical cup 57).

What is claimed is:

1. Spinal osteosynthesis device comprising at least two bone-anchoring elements (1; 31) for anchoring in respective bodies (S, L5) of the bone structure of the spine, at least one member (2; 16) for longitudinally connecting the bone-anchoring elements, and shackles (3) for connecting the bone-anchoring elements together, each bone-anchoring element comprising a head (5; 33) for grasping with a screwing tool (6), a threaded shank (7) extending the head for grasping, and a tightening element (8) which can be fitted onto this shank to immobilize the assembly comprising the connector shackle, the longitudinal connecting member and the corresponding bone-anchoring element, characterized in that the threaded shank (7) has a ball end (11) for articulation in a housing (12) of a spherical cup (57) of the head (5) for grasping, allowing the shank (7) to be oriented in many directions, and allowing the connecting shackle (3) to be positioned to suit the configuration of the vertebral segment (S, L5, . . . L2) receiving the bone-anchoring element, and in that the ball (11) and [the cup (57)] *an exterior surface of the head* have respective centres of rotation (R1, R2) which are separated by a distance (S), giving the device, when tightened using the tightening element (8), by bearing against the [spherical cup (57)] *exterior surface* of the head (5) for grasping, a function of returning the bone-anchoring element by transverse force, the connector shackle for this purpose having a spherical bearing surface (55) articulated to a portion of the spherical surface of the cup (57) of the head (5) of the bone-anchoring element.

2. Device according to claim 1, characterized in that the threaded shank (7) and the connecting shackle (3) are equipped with means for immobilizing the shank and its ball (11) in terms of rotation once the threaded shank has been introduced into a corresponding through-hole (10) through the shackle.

3. Device according to claim 2, characterized in that [the] said means *for immobilizing* [comprise] *comprises* at least one rotation-stopping geometry[, preferably two, namely] *comprising* a first rotation-stopping geometry (13) formed on a collar (14) arranged between the ball and the contiguous end of the threaded shank (7), and a second, female, rotation-stopping geometry (15) formed on the interior edge of the hole (10) in the shackle (3), this second rotation-stopping geometry being designed to press against the first rotation-stopping geometry once the shackle has been fitted on the threaded shank.

4. Device according to claim 1, characterized in that the opposite end of the threaded shank (7) to the ball (11) consists of a male shape (21)[, for example a half-moon shape,] designed to cooperate with a complementary female shape (23) of a tool (6) so as to immobilize the ball in terms of rotation while the tightening element (8) is being screwed onto the threaded shank (7).

5. Device according to claim 1, characterized in that the ball (11) is held in [its] *the* housing (12) by assembling [(for example screwing, crimping, welding, etc.)] the edge of the [latter] *housing* around the ball.

6. Device according to claim 1, characterized in that since the surface of the cup (57) of the head (5) is hemispherical and interrupted in the polar region to receive the ball (11), the associated spherical surface (55) of the shackle (3) at least partially covers the hemispherical surface of the cup, so as to produce either an effect of returning the bone-anchoring element (4) towards the axis, when coverage is total, as far as the equator of the cup, or a slight return, roughly maintaining the initial angular position of the bone-anchoring element, when coverage is only partial.

7. Device according to claim 6, characterized in that the connecting shackle (3) has a conical bearing surface (56) for the tightening element (8), this surface being connected to the said spherical surface (55).

8. Device according to claim 1, characterized in that it further comprises at least one bone-anchoring element (31) comprising a threaded anchoring shank (32), a head (33) which has a transverse collar (34) and a shape (35) for grasping, for screwing, and a threaded shank (7) extending the head, the assembly being all of one piece.

9. Device according to claim 1, characterized in that the threaded shank (7) has a narrowed portion (18) delimiting two threaded regions (17) and (19) of this shank and constituting an initiator for breakage once the tightening element has been assembled and fitted on the connecting shackle, this narrowed portion therefore allowing the shank (7) to be broken.

10. Device according to claim 1, characterized in that the member for longitudinally connecting the bone-anchoring elements (1) is a vertebral rod (2) passing through the shackles (3) for connecting to the bone-anchoring elements.

11. Device according to claim 1, characterized in that the member for longitudinally connecting the bone-anchoring elements (1) and (31) is a plate (16) in which there are formed cylindrical and/or oblong openings (41, 43) delimiting possible locations for the bone-anchoring elements and through which the threaded shanks (7) on which the immobilizing tightening elements (8) are fitted pass, and in that the openings in the plate (16) have a similar outline to that of the hole (10) in the connecting shackle (3) so as likewise to fulfil a function of returning the bone-anchoring element.

12. Device according to claim 1, characterized in that it comprises a system for transversely connecting the bone-anchoring elements (1), this system being formed of a pair of dished elements (58, 59) each of one piece with a tab (61, 62), the relative position and therefore the separation between the dished elements being adjustable for example by means of a screw-nut assembly (63, 64) passing through an elongate slot (65) in one tab (61) and a tapped hole in the second tab (62).

13. A system for installing bone anchoring element, comprising:

a spinal osteosynthesis device comprising at least two bone-anchoring elements (1; 31) for anchoring in respective bodies (S, L5) of the bone structure of the spine, at least one member (2; 16) for longitudinally connecting the bone-anchoring elements, and shackles (3) for connecting the bone-anchoring elements together, each bone-anchoring element comprising a head (5; 33) for grasping with a screwing tool (6), a threaded shank (7) extending the head for grasping, and a tightening element (8) which can be fitted onto this shank to immobilize the assembly comprising the connector shackle, the longitudinal connecting member and the corresponding bone-anchoring element, characterized in that the threaded shank (7) has a ball end (11) for articulation in a housing (12) of a spherical cup (57) for the head (5) for grasping, allowing the shank (7) to be oriented in many directions, and allowing the connecting shackle (3) to be positioned to suit the configuration of the vertebral segment (S, L5, . . . L2) receiving the bone-anchoring element, and in that the ball (11) and [the cup (57)] *an exterior surface of the head* have respective centers of rotation (R1, R2) which are separated by a distance (S), giving the device, when tightened using the tightening element (8), by bearing against the [spherical cup (57)] *exterior surface* of the head (5) for grasping, a function of returning the bone-anchoring element by transverse force, the connector shackle for this purpose having a spherical bearing surface (55) articulated to a portion of the spherical surface of the cup (57) of the head (5) of the bone-anchoring element; and a tool (6) for angularly positioning the threaded shank (7) and its ball (11) in the shackle (3) or the plate (16), comprising a sleeve (24) mounted to slide axially inside a socket (25), the end of which has a female shape (9) for screwing the tightening element while the end of the sleeve is provided with a female shape (20) designed to fit over a terminal male shape (21) of the threaded shank (7) so as to immobilize the threaded shank in terms of rotation in the position corresponding to the rotation-stopping geometry while the tightening element is being fitted using a cavity (9) of the socket (25).

*14. Spinal osteosynthesis device comprising:*

*at least two bone-anchoring elements; and*

*means for longitudinally connecting the at least two bone-anchoring elements;*

*each of the at least two bone-anchoring elements comprising:*

*a head shaped so as to allow grasping with a screwing tool;*

*a threaded shank extending from the head, and*

*a tightening element which can be fitted onto the threaded shank to immobilize an assembly comprising the means for longitudinally connecting and a corresponding one of said at least two bone-anchoring elements,*

*wherein the threaded shank has a ball end for articulation in a housing of a spherical cup of the head, allowing the shank to be selectively oriented with respect to the head, and wherein the threaded shank and the means for longitudinally connecting are constructed and arranged so that the shank and the ball are prevented from rotating once the threaded shank has been introduced into a corresponding through-hole through the means for longitudinally connecting.*

*15. Device according to claim 14, wherein the threaded shank comprises a first rotation-stopping geometry arranged between the ball and an opposite end of the threaded shank, and a second, female, rotation-stopping geometry is formed on an interior edge of the through-hole in the means for longitudinally connecting, this second rotation-stopping geometry being designed to press against the first rotation-stopping geometry once the means for longitudinally connecting has been fitted on the threaded shank.*

*16. Device according to claim 14, characterized in that an end of the threaded shank opposite the ball comprises a male shape designed to cooperate with a complementary female shape of a tool so as to allow immobilization of the ball in terms of rotation while the tightening element is being screwed onto the threaded shank.*

*17. Device according to claim 14, wherein the threaded shank has a narrowed portion delimiting two threaded regions of the shank, the narrowed portion constituting an initiator for breakage once the tightening element has been assembled and fitted on the means for longitudinally connecting, this narrowed portion therefore allowing the shank to be broken.*

*18. Device according to claim 14, wherein the threaded shank comprises two rotation-stopping geometries formed on a collar arranged between the ball and an opposite end of the threaded shank, and a two female rotation-stopping geometries are formed on an interior edge of the through-hole in the means for longitudinally connecting, the two rotation-stopping geometries of the through-hole being designed to press against the two rotation-stopping geometries of the threaded shank once the means for longitudinally connecting has been fitted on the threaded shank.*

*19. The spinal osteosynthesis device of claim 14, wherein the means for longitudinally connecting the at least two bone-anchoring elements comprises:*

*a shackle corresponding to each of the at least two bone-anchoring elements; and*

*a member that interconnects a plurality of the shackles.*

*20. The spinal osteosynthesis device of claim 14, wherein the means for longitudinally connecting the at least two bone-anchoring elements comprises:*

*a plate comprising a plurality of apertures, each of the apertures sized and shaped so as to allow engagement with a respective one of the bone-anchoring elements.*

*21. The spinal osteosyntheses device of claim 16, wherein each of the male end of the threaded shank and the complementary female end of the tool comprise a half-moon shape.*

*22. The spinal osteosyntheses device of claim 17, wherein the narrowed portion of the threaded shank comprises a rotation-stopping geometry.*

*23. The spinal osteosyntheses device of claim 22, wherein the end of the threaded shank opposite the ball comprises a male shape designed to cooperate with a complementary female shape of a tool so as to allow immobilization of the ball in terms of rotation, and wherein a cross-sectional shape of the male shape is the same as a cross-sectional shape of the narrowed portion of the threaded shank with the rotation-stopping geometry.*

*24. A spinal osteosynthesis device comprising:*

*at least two bone-anchoring elements; and*

*an interconnecting element that interconnects the at least two bone-anchoring elements;*

*each of the at least two bone-anchoring elements comprising:*

*a head shaped so as to allow grasping with a screwing tool;*

*a threaded shank pivotably connected to the head, the threaded shank terminating in a ball positioned in a socket on the head; and*

*a tightening element which can be fitted onto the threaded shank to immobilize an assembly comprising the interconnecting element and a corresponding one of said at least two bone-anchoring elements,*

*wherein the threaded shank and the interconnecting element are constructed and arranged so that the shank and the ball are prevented from rotating once the threaded shank has been introduced into a corresponding through-hole in the interconnecting element.*

*25. A spinal osteosynthesis device comprising:*

*at least two bone-anchoring elements, each comprising a head having a shape to allow grasping with a screwing tool, a threaded shank extending from the head, the threaded shank terminating in a ball that is pivotally disposed in a socket in the head, and a tightening element that can be threaded onto the shank;*

*at least one longitudinal member; and*

*shackles structured to engage the at least one longitudinal member and the at least two bone-anchoring elements, each said shackle comprising an aperture through which the threaded shank can pass;*

*wherein the head of each said bone-anchoring element has a hemispherical outer surface, a spherical center of which lies as a distance from a spherical center of the socket in the head, each said shackle having a surface that conforms to the hemispherical outer surface of the head, such that when the tightening element is threaded onto the threaded shank to urge the conforming surface of the shackle against the hemispherical outer surface of the head, the threaded shackle is forced into an alignment position with respect to the head.*

* * * * *